United States Patent [19]

Baker et al.

[11] Patent Number: 5,604,110
[45] Date of Patent: *Feb. 18, 1997

[54] BINDING ASSAY DEVICE

[75] Inventors: Terence S. Baker, Staines; Martin J. Perry, New Malton; Ian M. Fleming, Merseyside, all of England

[73] Assignee: Celltech Therapeutics Ltd., Berkshire, England

[ * ] Notice: The term of this patent shall not extend beyond the expiration date of Pat. No. 5,500,350.

[21] Appl. No.: 488,080

[22] Filed: Jun. 7, 1995

Related U.S. Application Data

[63] Continuation of Ser. No. 235,261, Apr. 29, 1994, Pat. No. 5,500,350, which is a continuation of Ser. No. 83,329, Jun. 29, 1993, abandoned, which is a continuation of Ser. No. 702,128, May 16, 1991, abandoned, which is a continuation of Ser. No. 347,725, May 5, 1989, abandoned, which is a continuation of Ser. No. 80,565, filed as PCT/GB86/00670, Oct. 30, 1986, abandoned.

[30] Foreign Application Priority Data

Oct. 30, 1985 [GB] United Kingdom .................. 8526741

[51] Int. Cl.$^6$ ..................................................... G01N 33/53
[52] U.S. Cl. .......................... 435/7.92; 422/56; 435/7.93; 435/7.94; 435/805; 435/962; 435/970; 436/514; 436/518; 436/810; 436/817
[58] Field of Search .......................... 422/56; 435/7.92, 435/7.93, 7.94, 28, 805, 806, 962, 970; 436/501, 514, 518, 535, 810, 817

[56] References Cited

U.S. PATENT DOCUMENTS

| | | | |
|---|---|---|---|
| 4,110,079 | 8/1978 | Schaeffer et al. | 422/56 |
| 4,361,537 | 11/1982 | Deutsch et al. | 422/56 |
| 4,446,232 | 5/1985 | Liotta | 436/515 |
| 4,690,970 | 9/1987 | Hibino et al. | 436/524 |
| 4,740,468 | 4/1988 | Weng et al. | 436/501 |
| 4,857,453 | 8/1989 | Ullman et al. | 435/7.92 |
| 4,861,711 | 8/1989 | Friesen et al. | 435/7.92 |
| 4,956,275 | 9/1990 | Zuk et al. | 435/7.92 |
| 4,960,691 | 10/1990 | Gordon et al. | 435/6 |
| 5,500,350 | 3/1996 | Baker et al. | 435/7.92 |

FOREIGN PATENT DOCUMENTS

| | | |
|---|---|---|
| 1183080 | 2/1985 | Canada . |
| 0030684 | 6/1981 | European Pat. Off. . |
| 0088636 | 9/1983 | European Pat. Off. . |
| 2514511 | 4/1985 | France . |
| 3445816 | 6/1986 | Germany . |
| 2116318 | 9/1983 | United Kingdom . |

*Primary Examiner*—Paula K. Hutzell
*Assistant Examiner*—Susan C. Wolski
*Attorney, Agent, or Firm*—Spencer & Frank

[57] ABSTRACT

A device for performing an enzyme-labelled binding assay comprises an absorbent material and a developing solution, wherein the absorbent material is provided with a plurality of reagent zones including an indicator reagent zone, and is capable of transporting the developing solution by capillary action sequentially through each reagent zone, and wherein the indicator reagent zone includes a reagent capable, directly or indirectly, of immobilizing an enzyme-labelled reagent in an amount dependent upon the assay result, characterized in that the developing solution includes a signal producing substrate for the enzyme. The substrate moves slower through the absorbent material than the enzyme-labelled reagent or any compound of the enzyme-labelled reagent formed in the assay. The absorbent material is suitably in the form of an elongate strip provided with transverse reagent zones. The device is useful form performing immunoassays including immunometric assays and dual analyte assays.

6 Claims, 3 Drawing Sheets

BINDING ASSAY DEVICE

This is a continuation of application Ser. No. 08/235,261 filed Apr. 29, 1994, now U.S. Pat. No. 5,500,350, which is a continuation of Ser. No. 08/083,329 filed Jun. 29, 1993, now abandoned, which is a continuation of Ser. No. 07/702,128 filed May 16, 1991, now abandoned, which is a continuation of Ser. No. 07/347,724 May 5, 1989, now abandoned, which is a continuation of Ser. No. 07/080,565, filed as PCT/GB86/00670, Oct. 30, 1986, now abandoned.

FIELD OF THE INVENTION

This invention relates to a device for performing an enzyme-labelled binding assay, the device comprising an absorbent material and a developing solution, wherein the absorbent material is provided with a plurality of reagent zones including an indicator reagent zone and is capable of transporting the developing solution by capillary action sequentially through each reagent zone, and wherein the indicator reagent zone includes a reagent capable, directly or indirectly, of immobilising an enzyme-labelled reagent in an amount dependent upon the assay result.

BACKGROUND TO THE INVENTION

Binding assays such as immunoassays, are in widespread use in clinical laboratories for the detection of substances in biological fluids. There is however increasing interest in the development of assays which can be performed without the need for complex analytical techniques and equipment, for example, by a physician in his consulting room or by a patient at home. Such assays are not only more convenient but allow savings in time and expense. Particular applications for which convenient and simple assays and reagent formulations are being sought are the detection of pregnancy and of the fertile period of the menstrual cycle.

It is known to conduct binding assays on a strip of material provided with a plurality of reagent zones, in which a developing solution forms a solvent front which passes along the strip by capillary action picking up and facilitating reaction between a sample and assay reagents located at the reagent zones (see for example, British patent specification GB-B-1589234). A feature of such strips is the existence of a test location at which, under certain conditions determined by the assay protocol and the sample composition, a labelled reagent becomes immobilised, giving an indication of the assay result. In early assays, the labelled reagent was a binding partner or analogue of the analyte to be measured, labelled with a radioactive isotope. Such assays require instrumentation to detect the level of radioactive label and may present health risk problems. A solution to this has been the use of enzyme labels which produce a characteristic signal (such as a colorimetric signal) with an appropriate substrate.

A significant problem in the design of such so called "dipstick" enzyme-labelled binding assays is the application of the appropriate enzyme substrate in order to produce a detectable signal. The signal may be developed by adding substrate to the appropriate position on the reagent strip after allowing the assay to proceed to completion. Alternatively, the appropriate part of the strip may be removed and chemically analysed. All of these represent steps which would be at least inconvenient, if not impossible for home use of the assay.

SUMMARY OF THE INVENTION

According to the present invention, we provide a device for performing an enzyme-labelled binding assay, the device comprising an absorbent material and a developing solution, wherein the absorbent material is provided with a plurality of reagent zones including an indicator reagent zone, and is capable of transporting the developing solution by capillary action sequentially through the reagent zones, and wherein the indicator reagent zone includes a reagent capable, directly or indirectly, of immobilising an enzyme-labelled reagent in an amount dependent upon the assay result, characterised in that the developing solution includes a signal-producing substrate for the enzyme.

The present invention, in its broadest concept, facilitates the use of binding assays in the home with the minimum of manipulative steps. As the solvent front of the developing solution passes through the absorbent material, picking up the reagents and allowing them to react, a signal, such as colour formation, occurs when the substrate contacts the enzyme-labelled reagent. This may result in a band of signal at the solvent front of the developing solution which passes up the test strip in the course of the assay. As the solvent front passes through a reagent zone in which the enzyme-labelled reagent is immobilised, a signal separation occurs as the bound enzyme-label is immobilised and unbound enzyme-label proceeds with the solvent front.

This separation, whilst adequate for many applications, may be unsatisfactory because the separation of the signal resulting from bound and unbound enzyme-labelled species is, under some binding conditions unclear. In a colorimetric assay this may result in smearing of the colour signal and obscurity in the assay result.

Preferably, in a particularly advantageous form of the device, the developing solution includes a signal-producing substrate for the enzyme which substrate, in use, is transported by the developing solution slower than the enzyme-labelled reagent or any compound of the enzyme-labelled reagent formed in the assay.

The preferred form of the invention overcomes the further problem described above because transport of the enzyme substrate occurs slower than transport of the enzyme-labelled reagent. In use, the reactions involved in the assay take place in the moving solvent front as the developing solution passes through the absorbent material. The substrate is transported slower than the enzyme-labelled reagent and compounds formed during the assay reactions, which remain ahead of the substrate in the absorbent material. The assay result is given by immobilising the enzyme-labelled reagent, either directly or indirectly through another species. The enzyme-labelled reagent, thus immobilised, does not remain ahead of the substrate which subsequently comes into contact with any immobilised enzyme-labelled reagent thus generating a signal. Any enzyme-labelled reagent which is not immobilised remains ahead of the substrate and therefore colour smearing does not occur. In the absence of immobilised enzyme-labelled reagent, no signal is generated in the immobilising region of the absorbent material at any stage in the assay, not even transiently as the solvent front passes through the immobilising region. This is important, especially when the device is intended for home use, to show a clear result. The invention provides a significant improvement to the sensitivity and clarity of dip stick assays.

The signal-producing substrate may be a single colour-producing compound or may be a compound acting as a cofactor with a further compound or compounds to produce a coloured signal in the presence of enzyme. The further compound or compounds may be included in the developing solution and may either be included in the developing solution and may either be transported by the developing solution with, or more slowly than, the enzyme-labelled reagent or any compound of the enzyme-labelled reagent formed in the assay. For example, the substrate may be tetramethylbenzidine which is oxidised by hydrogen peroxide in the presence of a peroxidase to produce a coloured signal.

The assay may be any type of enzyme-labelled binding assay in which the amount of an enzyme-label immobilised in an indicator reagent zone is indicative of the result of the assay. The signal produced in the indicator reagent zone is preferably colorimetric. The device is suitable for conducting competitive and non-competitive binding assays in which analyte in the sample either binds to an enzyme-labelled reagent or binds to an enzyme-labelled reagent in competition with an analyte analogue. Preferably the assay is an immunoassay.

The assay may be for example a two site immunometric assay or a dual competition assay such as a dual analyte assay of the type described in published British specifications GB-B-2029011 and GB-B-2116313. The analyte may be any analyte which has a specific binding partner.

The absorbent material, which may be in the form of an elongate strip, may be any material capable of transporting the developing solution by capillary action. A preferred material is a bibulous paper, such as a glass fibre paper, although any material exhibiting the necessary capillary property and a low level of non-specific binding could be used.

Differential migration of the enzyme-labelled species and the substrate may be achieved by selection of appropriate materials for the absorbent material given particular combinations of enzyme-label, substrates and buffers. Compounds may be added to the paper to modify the differential transport properties of the paper. In particular, a compound or compounds may be added to the paper to increase attractive interactions between the paper and the substrate relative to interactions between the paper and the enzyme-labelled species. For example, where the substrate is tetramethylbenzidine (TMB) and the paper is a borosilicate glass fibre paper, an acrylic binder incorporated in the glass fibre during manufacture reduces the migration rate of TMB markedly. Conversely certain compounds such as B-cyclodextrin interfere with the interaction and reduce the attraction effect of such binders. We have demonstrated that, on a strip of glass fibre composed of pure borosilicate glass, peroxidase, $H_2O_2$ and TMB migrate with the solvent front (Rf=1.0) when an aqueous developing buffer such as 0.1M acetate (pH 6.0) containing 0.2% Tween 20 is employed. However, when an acrylic binder is included in the manufacture of the borosilicate glass fibre, the migration of $H_2O_2$ and peroxidase is unaltered but the migration rate of TMB is reduced (Rf less than 1.0). The Rf value of the TMB can thus be controlled to the desired value by the concentration of acrylic binder present in the glass-fibre. The differential migration of TMB on glass-fibre containing an acrylic binder can also be controlled by the use of a compound which interferes with the interaction between the TMB and the acrylic binder, e.g. B-cyclodextrin. For example, if a strip of Gelman AP25 extra thick glass-fibre paper (Gelman Sciences Inc., Ann Arbour, Mich., USA) is placed into a solution containing 0.1M acetate (pH 6.0), 0.1 mgml$^{-1}$ TMB, 0.001% $H_2O_2$ 1% DMSO and 0.2% Tween 20, the TMB migrates with an RF value of 0.4. Inclusion of B-cyclodextrin in the developing solution at 0.1% (w/v) increases the Rf value of TMB to 0.55 with no effect on the $H_2O_2$. Increasing the B-cyclodextrin concentration to 0.25% (w/v) increases the Rf value of TMB to 0.7 with no effect on the $H_2O_2$. In addition, B-cyclodextrin has no effect on the migration of peroxidase which migrates with the buffer front (Rf=1.0).

Alternatively, differential migration of the enzyme-labelled species and the substrate may be achieved by providing a substrate binding reagent zone, capable of binding the substrate at a location on the assay device encountered, in use, by the developing solution prior to the enzyme-labelled reagent zone, such that, in use, the substrate is prevented from passing through the said binding reagent zone until the binding reagent zone is substantially saturated.

The reagent zones on or in the absorbent material are arranged such that the developing solution contacts them sequentially. The reagent zones include the reagents for the particular assay protocol and may be arranged on or in the material to allow for a predetermined incubation period between contact with adjacent reagent zones.

The spacing of the reagent zones provides a parameter which may be varied to set the predetermined incubation period. Alternatively the migration rate of the developing solution may be controlled or modified by the inclusion of a compound, such as a polymer, into the developing solution. Suitable such polymers include dextran or polyvinylpyrrolidine which cause a reduction in the migration rate. The compound capable of modifying the migration rate of the developing solution (for example a polymer) may be provided in a further reagent zone immediately following a given reagent zone such that, in use, the migration of reagents in the solvent front will be temporarily halted or delayed at the given reagent zone whilst the compound at the further reagent zone is solubilised. Thus, by halting migration of the developing solution at a given reagent zone, more time is provided for incubation at that zone.

In the preferred form of the device, the absorbent material is in the form of an elongate strip with transverse reagent zones.

Preferably the cross-sectional area of the absorbent material in at least part of the indicator zone is smaller than the cross-sectional area of the absorbent material in the rest of the device. Where the absorbent material is in the form of a strip this may advantageously be achieved by forming a neck in the strip of the indicator reagent zone. This provides the additional advantage of concentrating all the reagents passing up the strip of the reagent zone, thus increasing the potential signal intensity.

The developing solution may be the sample itself to which substrate is added, but is preferably separate from the sample. Advantageously it is contained in a rupturable sac adjacent part of the absorbent material, suitably at one end of a strip of absorbent material. In the alternative, the device of the invention may be in the form of a kit comprising separately an absorbent material and a container of the developing solution, as defined. Preferably, the developing solution comprises a buffer compatible with the assay system. A particularly preferred developing solution for an enzyme-labelled immunoassay comprises 0.1M acetate (pH 6) containing 0.2% (v/v) Tween 20 and the enzyme substrate, as appropriate. The developing solution may, in addition, include a compound capable of modifying the migration rate of the developing solution, such as a polymer, for example dextran or polyvinylpyrrolidone.

The enzyme may be any enzyme capable of producing a measurable signal in the presence of an appropriate substrate. For example the enzyme may be horseradish peroxidase and the developing solution may contain tetramethylbenzidine (TMB) and hydrogen peroxide.

The device may include a sample receiving zone which can, if desired, be provided with a filter member, such as a filtration pad, to remove solid material such as cellular material and debris.

In order that the physical dimensions of the absorbent material are not excessive, the enzyme-labelled reagent (in its free and bound states) should preferably exhibit an $R_f$ value of not less than 0.7. Preferably the $R_f$ value of the enzyme substrate should be in the range 50 to 90% that of the enzyme-labelled species (in its free and bound states).

The device of the invention may include an assay completion indicator zone comprising immobilised enzyme to indicate completion of the assay. Where the absorbent material is in the form of a strip, the assay completion indicator zone is preferably located near the end of the strip remote from the end at which the developing solution is applied.

The absorbent material may be enclosed within a non-transparent covering except in the indicator reagent zone where a transparent window may be provided. Access to the sample zone may be provided by removal of a resealable plug which can be replaced after application of the sample. Application of a sample to the device may be by way of an applicator which delivers a predetermined volume of the sample, for example a sampling loop.

The device may be individually packages, but for easy monitoring of the menstrual cycle, for example for home use, a plurality of devices of the invention may be packages together. We further provide therefore a test sheet comprising a plurality of devices of the invention.

In use, the developing solution is applied to the absorbent material. For example, where the absorbent material is in the form of a strip, the developing solution is applied to one end of the strip, advantageously by rupturing a sealed sac, for example, by finger pressure, to release the contents. The developing solution advances through the absorbent material, picking up sample applied at the sample receiving zone, and other reagents including an enzyme-labelled reagent. The enzyme substrate or a cofactor included in the developing solution, travels through the absorbent material more slowly than the enzyme-labelled reagent and no signal is therefore produced. The assay reactions take place in the advancing solvent front of the developing solution and after an incubation period determined by the separation of the reagent zones, an amount of the enzyme-labelled reagent is immobilised in the indicator reagent zone in an amount dependent upon the assay result. The substrate then comes into contact with the immobilised enzyme-labelled reagent, thereby generating a signal in the indicator reagent zone.

The result of an assay as indicated by the device of the invention may be qualitative, read simply by the absence or presence of a signal, especially a coloured signal at the indicator reagent zone. This type of result may be, for example, of considerable use where a threshold value of a particular analyte in a sample is being monitored (such as the level of a particular hormone). However, the device can be employed to provide quantitive assay results. The intensity of the signal produced at the indicator reagent zone will be either proportional to or inversely proportional to the concentration of analyte present in the sample. Thus, the indicator reagent zone of the device may, following an assay, be inserted into a reflectance spectrophotometer, or a fluorimeter (if the signal produced is fluorescent), to measure the intensity of the signal produced. Alternatively, the indicator reagent zone may be elongated in the direction of developing solution migration or a plurality of individual indicator reagent zones may be provided. Thus, the length of signal produces at the indicator reagent zone or the number of individual zones which exhibit the signal will be quantitative and proportional to, or inversely proportional to, the concentration of analyte present in the sample.

BRIEF DESCRIPTION OF THE DRAWINGS

The invention is now described by way of example with reference to the accompanying drawings in which.

Embodiments of the invention are described first generally with reference to FIGS. 1 to 6 and then more specifically with reference to specific Examples 1 to 4.

The following description of materials and methods to the general embodiments described below and specifically to Examples 1 and 4 below.

Unless otherwise states, all reagents were obtained from Sigma Chemical Company, Poole, U.K.

ABSORBENT STRIP MATERIAL

Gelman AP25 extra thick glass-fibre paper (from Gelman Sciences Inc., Ann Arbor, Mich., U.S.A.)

DEVELOPING SOLUTION (SUBSTRATE BUFFER)

The developing solution was prepared as follows:
To 1000 ml of sterile $DH_2O$ was added:

|  |  |
| --- | --- |
| 2.5 g | B-cyclodextrin |
| +8.2 g | sodium acetate |
| +0.357 g | citric acid |
| +50 ul | 30% $H_2O_2$ |
| +10 ml | of TMB in DMSO at 10 mg/ml |
| +5 g | of BSA * |
| +1 ml | Tween 20 |
| +5 g | sodium chloride |

* Sigma Chemical Company No. A8647, Fraction V

SOLID-PHASE ANTIBODY

Reagent immobilisation on the strip, may be accomplished by physical adsorption or chemical coupling to the strip using techniques well known in the art (see R. Axen et al, (1967), Nature, 214, 1302; S. Avrameas and T. Ternynck, (1969), Immunochemistry, 6, 53; G. S. Bethell et al, (1979), The Journal of Biological Chemistry, 254, 2672; J. M. J. Frechet, (1981), Tetrahedron, 37, 663).

A preferred technique is however to attach the ligand to an insoluble particle which is of the correct size to be trapped within the framework of the absorbent strip material and thus unable to move with the developing solution. A suitable type of particle is Eupergit Clz, supplied by Rohm Pharma GmBH, Weiterstadt, West Germany. The coupling of antibodies to this material is described below:

Buffer A. To 1000 ml of DH$_2$O was added:

| |
|---|
| 5.96 g Na$_2$HPO$_4$ |
| +1.24 g NaH$_2$PO$_4$ |
| +29.22 g NaCl |

To 500 µl of the above buffer (A) was added 3–4 mg of freeze-dried antibody and 125 mg of Eupergit Clz. The reagents were mixed briefly and then left to stand at room temperature for 48 hours. The Eupergit was then resuspended in 20 ml of the following buffer (Buffer B).

Buffer B. To 1000 ml of DH$_2$O was added:

| |
|---|
| 5.96 g Na$_2$HPO$_4$ |
| +1.24 g NaH$_2$PO$_4$ |
| +3.75 g Glycine |

The Eupergit Clz was allowed to settle at 4° C. for 12 hours. The supernatant was then aspirated off, and the Eupergit then resuspended in 20 ml of Buffer B and again allowed to settle. The supernatant was then again aspirated off, and the Eupergit/antibody resuspended in 12.5 ml of Buffer B.

ANTIBODY-PEROXIDASE CONJUGATE

The peroxidase conjugate may be prepared using, for example, sulfhydrylmaleimide coupling (Ishikawa, E., (1980), Immunoassay suppl, 1, 1–16; Duncan, R. J. S. et al, Anal. Biochem., 132, 68–72), disulphide-thiol exchange (Carlsson, J., et al, (1978), Biochem, J., 173, 723–737), periodate oxidation (Nakane, P. K., et al (1974), J. Histochem. Cytochem, 22, 1084–191) or glutaraldehyde coupling (Avrameas, S. (1969), Immunochem., 7, 43–72; Avrameas, S., et al, (1971), Immunochem, 8, 1175–1179).

In the preferred method, horseradish peroxidase (HRP) was conjugated to a monoclonal antibody using an adaptation of the glutaraldehyde method of Avrameas (loc. cit.). 100 mg of HRP was dissolved in 500 ul of 0.05M bicarbonate buffer (pH 9.5) to which was added 500 ul of 11% (w/v) glutaraldehyde prepared in the same buffer. The reaction was conducted at room temperature (20° C.–25° C.) for two hours with gentle shaking. The reaction mixture was then applied to a PD10 column (Pharmacia Ltd.) which had previously been equilibrated with 0.05M bicarbonate buffer (pH 9.5). Elution was achieved with the same buffer and those fractions containing activated HRP were pooled. Antibody (2–3 mg/ml) in 0.05M bicarbonate buffer (pH 9.5) was added to the activated HRP to give a mass ratio of 6:1 of activated HRP to antibody. The reaction was conducted at 4° C. for 16–21 hours after which the antibody-HRP conjugate was purified by gel filtration, typically on a TSK G3000SW column (Toya Soda, Japan).

MIXED STEROID ANTIGEN (MSA)

Mixed steroid antigen (MSA) is a bifunctional ligand comprising oestrone-3-glucuronide (El3G) and pregnanediol-3-glucuronide (PD3G). The synthesis of the compound is described in British patent specification GB-B-2116318.

BUFFER C

To 1000 ml of sterile DH$_2$O was added:

| |
|---|
| 8.2 g sodium acetate |
| 0.357 g citric acid |
| 2 ml Tween 20 |

Figure 1:
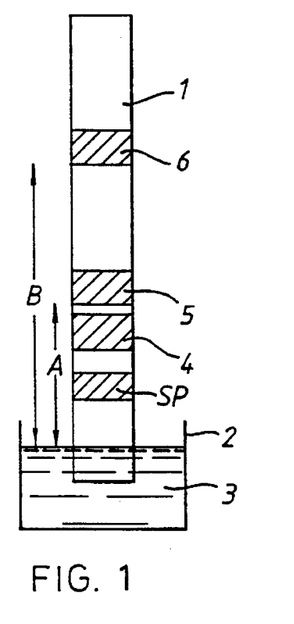
FIG. 1 shows a device for conducting a competitive hapten assay.

FIG. 1 shows a device for measuring the concentration of pregnanediol-3-glucuronide (PD3G) in a urine sample using a competitive hapten assay protocol. Referring to FIG. 1, the device comprises a strip, 1, of a bibulous paper and a reservoir, 2, containing a developing solution, 3, consisting of a substrate-buffer. The strip is provided with a sample receiving zone, 4, a first reagent zone, 5, and a second, indicator, reagent zone, 6. The first reagent zone, 5, includes enzyme-labelled PD3G hapten covalently attached to a horseradish peroxidase enzyme-label, the enzyme-labelled PD3G being impregnated into the strip, such that, in use, it is caused to migrate through the strip by passage of the developing solution through the strip. The indicator zone, 6, comprises antibody to PD3G covalently bonded to the strip. The reservoir, 2, consists of a rupturable sac containing the substrate buffer which includes the cofactors tetramethylbenzidine and hydrogen peroxide. In use, a sample of urine is applied to the sample receiving zone, 4, and the substrate buffer, 3, is released onto the end of the strip by rupturing the sac, 2, with finger pressure. The developing solution, 3, passes through the strip by capillary action picking up the sample and the enzyme-labelled PD3G in the solvent front from the sample receiving zone, 4, and the first reagent zone, 5, respectively. The enzyme cofactor, tetramethylbenzidine, is carried through the strip more slowly than the enzyme-labelled PD3G. Thus, when the solvent front of the substrate buffer, 3, reaches the first reagent zone, 5, little or no cofactor is present in the solvent front and substantially no colour formation occurs. Any PD3G present in the sample competes with the enzyme-labelled PD3G for a limited number of binding sites in the second, indicator, reagent zone, 6. The amount of enzyme-labelled PD3G that becomes bound to the strip in the indicator reagent zone, 6, is therefore inversely proportional to the concentration of PD3G in the sample. Continued development of the strip washes any unreacted reagents through the indicator zone, 6, and subsequently brings the cofactor into contact with the indicator zone where the substrate is converted by the bound enzyme-labelled PD3G to give a coloured product (horseradish peroxidase catalyses the oxidation of tetramethylbenzidine by hydrogen peroxide). The coloured product does not migrate further, thus giving a sharp band of colour at the indicator zone, 6. The difference between distances B and A as shown in FIG. 1 is made relatively small as the sample and the enzyme-labelled PD3G do not interact until the indicator zone, 6, is reached thus allowing a reduction in the length of the strip. However, the distance B must be sufficient to permit adequate washing of the bound enzyme-labelled PD3G by continued migration of the developing solution, 3, prior to the arrival of the cofactor at the indicator zone, 6. The duration of the competitive reaction which occurs at the indicator zone, 6, is equal to the time it takes for the sample and the enzyme-labelled PD3G to pass through the indicator zone, 6. This is determined by the physical properties of the material from which the strip is made.

Figure 2:
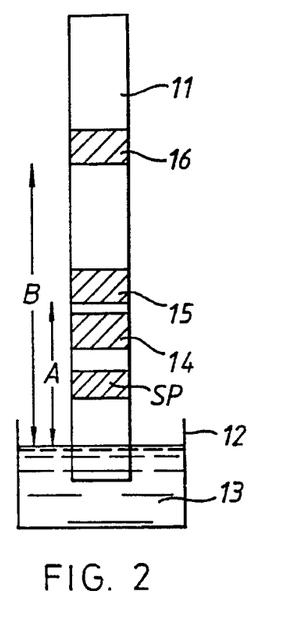
FIG. 2 shows a device for conducting a non-competitive hapten assay.

FIG. 2 shows a further device for measuring the concentration of PD3G in a urine sample using a non-competitive hapten assay protocol. Referring to FIG. 2, the device comprises a strip, 11, of a bibulous paper and a reservoir, 12, containing a developing solution, 13 consisting of a substrate-buffer. The strip is provided with a sample receiving zone, 14, a first reagent zone, 15, and a second, indicator, reagent zone, 16. The first reagent zone, 15, includes enzyme-labelled anti-PD3G comprising antibody to PD3G covalently attached to a horseradish peroxidase enzyme-label, the enzyme-labelled anti-PD3G being impregnated into the strip such that, in use, it is caused to migrate through the strip by passage of the substrate-buffer, 13, through the strip. The indicator zone, 16, comprises PD3G covalently bonded to the strip. The reservoir, 12, is as described above with reference to FIG. 1.

In use, a sample of urine is applied to the sample receiving zone, 14, and the substrate-buffer, 13, is released onto the end of the strip by rupturing the sac, 12, with finger pressure. The substrate buffer, 13, passes through the strip by capillary action picking up the sample. Any PD3G present in the sample is bound in the first reagent zone, 15, by the enzyme-labelled anti-PD3G which is present in excess. The incubation time for this interaction to take place is controlled by the difference between distances B and A as shown in FIG. 2. As the solvent front contacts the indicator zone, 16, PD3G covalently bonded to the strip binds any unreacted enzyme-labelled antibody to PD3G. Again, since the cofactor travels more slowly through the strip than the enzyme-labelled antibody, colour generation only occurs at the indicator zone, 16, where the enzyme-labelled antibody has been immobilised.

Figure 3:
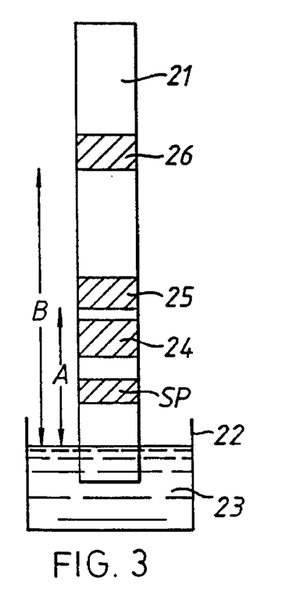
FIG. 3 shows a device for conducting a two-site sandwich, or immunometric assay.

FIG. 3 shows a device for measuring the concentration of thyroid stimulating hormone (TSH) in a sample using a two-site sandwich assay or immunometric assay protocol. Referring to FIG. 3 the device comprises a strip 21 of a bibulous paper and a reservoir, 22, containing a developing solution, 23 consisting of a substrate-buffer. The strip is provided with a sample receiving zone, 24, a first reagent zone, 25, and a second, indicator, reagent zone, 26. The first reagent zone, 25, includes enzyme-labelled anti-TSH comprising antibody to TSH covalently attached to a horseradish peroxidase enzyme-label, the enzyme-labelled anti-TSH being impregnated into the strip, 21, such that, in use, it is caused to migrate through the strip by passage of the substrate-buffer, 23. The indicator zone, 26, comprises a second antibody to TSH covalently bonded to the strip, 21. The second antibody has specificity for a different and non-competing epitope of TSH from that of the enzyme-labelled antibody. In use, any TSH present in the sample is bound by the enzyme-labelled antibody which is present in excess as they co-migrate through the strip. The time allowed for this first reaction is governed by the difference between the distances B and A as shown in FIG. 3. On passing through the indicator zone, the TSH (in the form of an antibody complex) is bound by the second antibody. The time of the second incubation is governed by the speed of capillary migration of the solvent front through the material of the strip. Again, colour development only occurs where the enzyme-labelled antibody is immobilised in the indicator zone thus allowing the cofactor to be brought into contact with it by the capillary motion of the solvent front.

Figure 4:
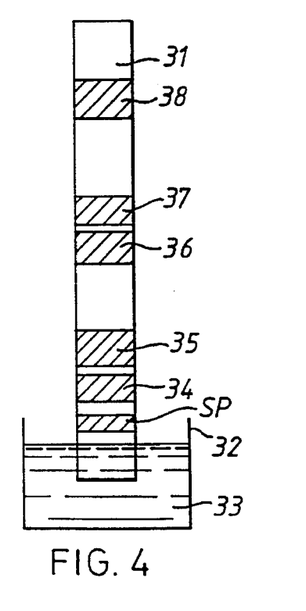
FIG. 4 shows a device for conducting a dual analyte assay.

FIG. 4 shows a device for measuring the ratio of the concentrations of PD3G and oestrone-3-glucuronide (El3G) in a urine sample. The ratio of these two products has been shown to be indicative of the fertile period of the female menstrual cycle (see for example British published specifications GB-B-2029011 and GB-B-2116318).

Referring to FIG. 4, the device comprises a strip, 31, of bibulous paper and a reservoir, 32, containing a developing solution, 33 consisting of a substrate-buffer. The strip is provided with a sample receiving zone, 34, a first reagent zone, 35, a second reagent zone, 36, a third reagent zone, 37, and a fourth, indicator, reagent zone, 38. The first reagent zone, 35, comprises a mixed steroid antigen (MSA) consisting of a PD3G hapten and an El3G hapten covalently bonded to a bridging structure. The MSA is impregnated into the strip, 31, such that, in use, it may migrate through the strip in the advancing solvent front of the substrate-buffer, 33. The second reagent zone, 36, comprises an antibody to El3G which may be free to migrate through the strip in the advancing solvent front though is preferably covalently bonded to the strip. The third reagent zone, 37, comprises an enzyme-labelled anti-El3G (antibody to El3G covalently attached to a horseradish peroxidase enzyme-label), impregnated into the strip, 31, such that it may migrate through the strip with the substrate-buffer, 33. The fourth, indicator, reagent zone, 38, comprises antibody to PD3G covalently bonded to the strip. The reservoir, 32, comprises a rupturable sac containing the substrate-buffer.

In use, a urine sample is applied to the sample zone, 34, and the reservoir, 32, of developing solution, 33, is ruptured, releasing the substrate-buffer onto one end of the strip. The substrate-buffer, 33, passes up the strip, 31, by capillary action picking up sample from the sample receiving zone, 34, and mixed steroid antigen from the first reagent zone, 35. The sample and the MSA co-migrate along the strip to the second reagent zone, 37, at which the antibody to El3G is covalently immobilised. The MSA and El3G present in the sample compete for limited binding sites as they pass through the second reagent zone, 36. If the concentration of El3G in the sample is low, then a substantial proportion of the MSA is bound in the second reagent zone, 36, and cannot migrate further. If, however, the sample concentration of El3G is high, then the MSA will be free to migrate, together with the sample, to the next reagent zone, namely, the third reagent zone, 37, comprising enzyme-labelled antibody to El3G. This latter reagent is present in excess and is non-covalently absorbed to the strip, 31. The enzyme-labelled antibody binds to the MSA as they both migrate together along the strip to the fourth, indicator, reagent zone, 38, at which antibody to PD3G is covalently attached to the strip. At the fourth indicator reagent zone, 38, any PD3G present in the sample competes with the MSA/anti-El3G complex for binding to a limited number of binding sites of the covalently immobilised anti-PD3G antibody. The enzyme-labelled immunocomplex will be bound at the indicator zone, 38, only when the sample concentration of PD3G is low. The excess reagents are washed from the measuring location by continued development of the strip. On reaching the indicator zone, 38, the cofactor is converted by the enzyme-labelled, antibody-bound MSA to a coloured product giving a clear positive signal. The assay can be tuned to give a positive response only when a predetermined elevated level of El3G coincides with a predetermined low level of PD3G. A further reagent zone (not shown) may be provided at a point remote from the reservoir, 32, which comprises covalently bound horseradish peroxidase. This reagent zone gives an indication that substrate has migrated through the length of the strip thus indicating that the assay has run to completion.

Figure 5:
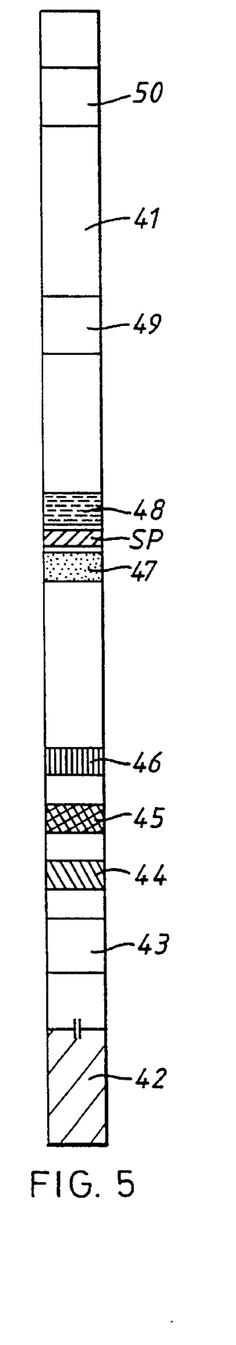
FIG. 5 shows a further device for conducting a dual analyte assay.

FIG. 5 shows a further device for measuring the ratio of the concentrations of PD3G and El3G in a urine sample.

Referring to FIG. 5, the device comprises a strip, 41, of bibulous paper and a reservoir, 42, containing a developing solution. The strip is provided with a sample receiving zone, 43, a first reagent zone, 44, a second reagent zone, 45, a third reagent zone, 46, a fourth reagent zone, 47, a fifth reagent zone, 48, a sixth, test indicator, reagent zone, 49 and an optional seventh, control indicator, reagent zone, 50. The first reagent zone, 44, comprises anti-El3G (antibody to El3G). The second reagent zone, 45, comprises a mixed steroid antigen (MSA) as described in Example 4. The third reagent zone, 46, comprises biotin-labelled anti-PD3G dextran-coated charcoal. The fifth reagent zone, (antibody to PD3G covalently bonded to biotin). The fourth reagent zone, 47, comprises 48, comprises enzyme-labelled anti-El3G (antibody to El3G covalently bound to horseradish peroxidase). The sixth reagent zone, 49, comprises immobilised streptavidin. The optional seventh reagent zone, 50, comprises horseradish peroxidase.

The active components of the reagent zones are dried onto the strip as transverse bands. The streptavidin in the sixth, test indicator, reagent zone, 49, is covalently attached to the strip and the dextran-coated charcoal in the fourth reagent zone, 47, is deposited onto the strip by adding an aqueous suspension of microparticulate charcoal and subsequently removing the water. All the other reagents are soluble and are impregnated into the strip by applying them each in solution and subsequently drying. The soluble reagents, in use, migrate with the solvent front of the developing solution. The reservoir, 42, comprises a rupturable sac containing the developing solution.

The use, a urine sample is applied to the sample receiving zone, 43, and the reservoir 42, of developing solution is ruptured, releasing the developing solution onto one end of the strip. The developing solution passes up the strip by capillary action, picking up sample from the sample receiving zone, 43, and, in sequence, anti-El3G, MSA and biotin-labelled anti-PD3G. The soluble components of the assay pass through the strip in the advancing solvent front, and at the same time are mixed and allowed to react. The separation of the reagent zones may be adjusted to facilitate optimum incubation times for reaction. Unbound, low molecular weight species such as MSA and steroids are removed from the solvent front by the charcoalin the fourth reagent zone, 47. The solvent front passes through the fifth reagent zone, 48, picking up enzyme-labelled anti-El3G, thus completing the assay protocol. The presence of complexes of enzyme-labelled anti-El3G/MSA/biotin-labelled PD3G is indicative of a high level of El3G and a low level of PD3G. Such complexes are immobilised in the sixth, test indicator, reagent zone, 49, by the interaction of biotin with immobilised streptavidin.

The developing liquid, as previously stated, includes a colour producing substrate for peroxidase. If the substrate has an $R_f$ value substantially the same as the enzyme-labelled species in the device, colour will develop in the solvent front as soon as the fifth reagent zone, 48, is reached and the solvent front will remain coloured for the rest of its passage through the strip. The presence of colour at the end of the strip remote from the developing solution indicates completion of the assay. As the solvent front meets and passes through the sixth, test indicator, reagent zone, 49, any coloured products and unbound enzyme-labelled anti-El3G will be washed clear of the zone by incoming fresh developing solution. However, if the complex including enzyme-labelled anti-El3G has become immobilised, colour generation occurs in the sixth, test indicator, reagent zone. Thus colour in the sixth reagent zone indicates a positive test result. Alternatively, if the substrate has an $R_f$ value less than the $R_f$ value of the slowest moving enzyme-labelled species, colour generation will only occur where an enzyme-labelled species is immobilised, i.e. in the sixth reagent zone when a positive result is obtained. In this alternative, which is preferred, a seventh, control indicator, reagent zone, 50, comprising horseradish corresponding to completion of the assay. peroxidase may be provided to indicate arrival of the substrate at a predetermined part of the strip, FIG. 6 shows a test sheet for monitoring the menstrual cycle embodying a plurality of test strips as described above with respect to FIGS. 4 or 5.

Figure 6:
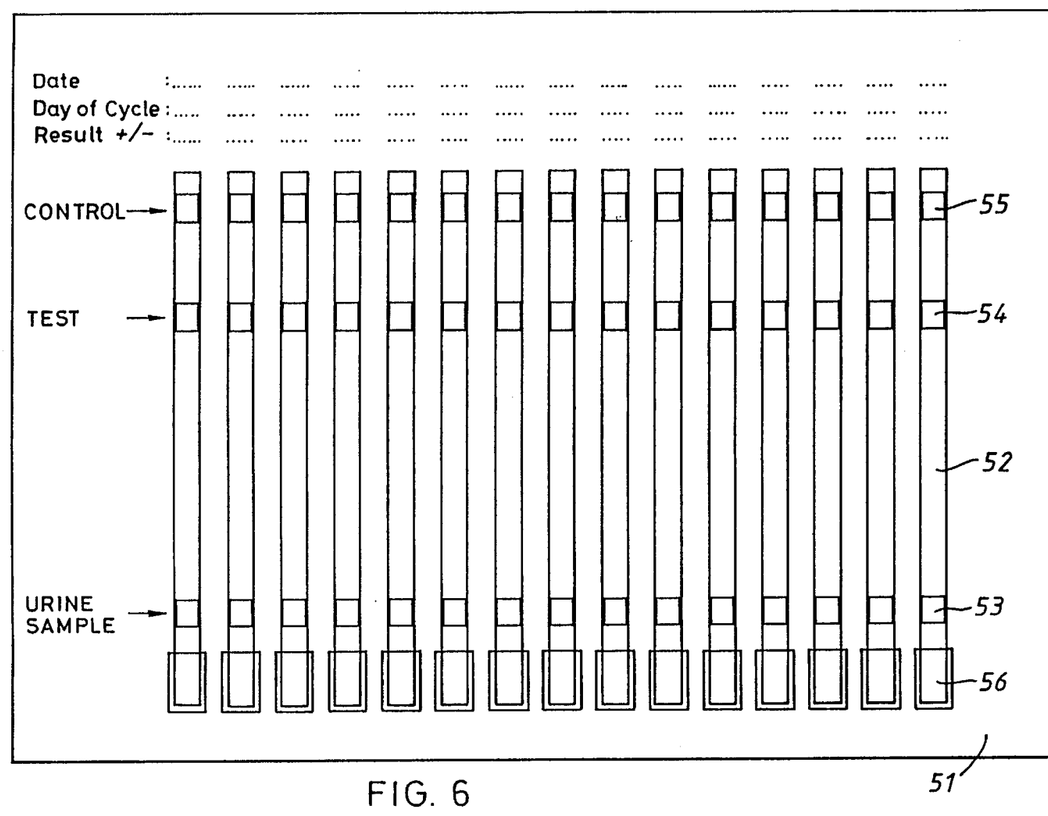
FIG. 6 shows test sheet comprising a plurality of devices of the invention arranged to monitor the menstrual cycle.

Referring to FIG. 6, the test sheet comprises a rigid plastics backing plate or stand, 51, supporting a plurality of test strips of the invention, e.g. 52 (In the Figure the details of the absorbent strips are not shown). In the embodiment shown, fifteen test strips are provided in side-by-side parallel arrangement. The backing plate or stand, 51, is overlaid with a plastics film, to cover the test strips, apart from in the sample receiving zone, 53. The plastics film (shown in FIG. 6 as transparent for clarity) is opaque save in the test indicator zones, 54, and in the control indicator zones, 55. The plastics film may be suitably masked or printed to indicate clearly the sample receiving, test indicator and control indicator zones. The developing solution is contained in separate rupturable sacs, 56, one for each test strip.

In use, mid-stream urine is sampled using a disposable sample loop and an aliquot is blotted onto the sample receiving zone, 53, of a test strip, 52. The seal of a rupturable sac, 56, of developing solution is broken by finger pressure, thus initiating the test. After 15 to 20 minutes, the control indicator zone, 55, is observed and, if coloured, the assay result is read from the test indicator zone, 54.

The presence of colour in the test zone indicates a positive result i.e. the woman is in, or near, her fertile period. The converse applies with the absence of colour. For the woman who wishes to avoid conception, it is intended that she should test her urine once per day starting at about day 6 or 7 of her cycle. She should continue daily testing until a period of sustained positive results have been observed (more than 2 days) followed by a period of sustained negative results (more than 2 days). This would normally mean a total of 10 to 15 tests in a typical cycle. Whenever a positive result is observed, the woman should refrain from intercourse and should continue to do so until two successive daily negative results have been observed.

It is intended that colours developed in the strips are stable, and so form a semi-permanent record of the woman's cyclical activity.

EXAMPLE 1

A device for conducting a competitive hapten assay similar to that described generally with respect to FIG. 1 was prepared.

Figure 7:
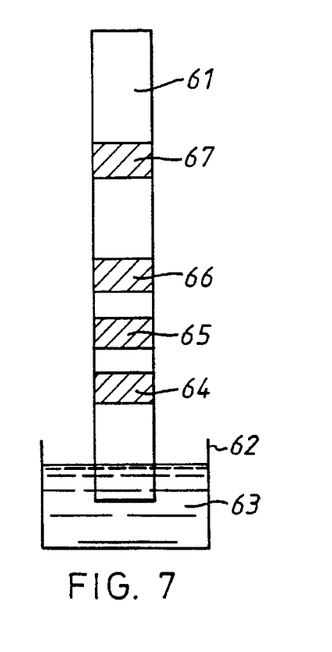
FIG. 7 shows a device for conducting a competitive hapten assay.

Referring to FIG. 7, the device comprises a strip of Gelman glass-fibre (15×1 cm), 61, and a reservoir, 62, containing the substrate-buffer, 63. The strip is provided with a sample receiving zone, 64, (1.5 cm from the lower end of the strip), a first reagent zone, 65, (2.0 cm from the lower end of the strip) to which has been applied 10 ul MSA (1000 nM in Buffer C), a second reagent zone, 66 (2.5 cm from the lower end of the strip) to which has been applied 10 ul of a monoclonal antibody to PD3G conjugated to peroxidase (1 ug ml$^{-1}$ in Buffer C) and an indicator zone, 67, (5.0 cm from the lower end of the strip) to which has been applied 50 ul of a solid phase monoclonal antibody to El3G.

In use, 20 ul of sample to be assayed for PD3G is applied to the sample receiving zone, 64, and the the strip is immersed. After 15 min, the indicator lower end of the strip is placed into 2 ml of substrate-buffer such that only the first 0.5 cm of zone, 67, observed. The presence of a blue colour at the indicator zone, 67, shows that the concentration of PD3G in the sample is less than 10000 nM. (colour at 5000 and 10000 nM: no colour at 15000, 20000 and 25000 nM)

The device operates as follows:

As the substrate-buffer migrates along the strip, PD3G in the sample, MSA and anti-PD3G peroxidase conjugate are transported at the buffer front together with all the components of the buffer-substrate except TMB which exhibits a slower rate of migration (Rf=0.7). During migration along the strip, the PD3G and MSA compete for the binding sites of the anti-PD3G peroxidase conjugate. On reaching the indicator zone, 67, the immobilised anti-El3G antibody binds to the MSA. If the concentration of PD3G in the sample is low, then the MSA will also be bound by the anti-PD3G peroxidase conjugate and when the TMB reaches the indicator zone, 67, a blue colour will be formed. If the concentration of PD3G in the sample is high, then the anti-PD3G peroxidase conjugate will not bind the MSA and no colour signal will be observed at the indicator zone, 67.

EXAMPLE 2

A device for conducting a non-competitive hapten assay similar to that described generally with respect to FIG. 2 was prepared.

Figure 8:
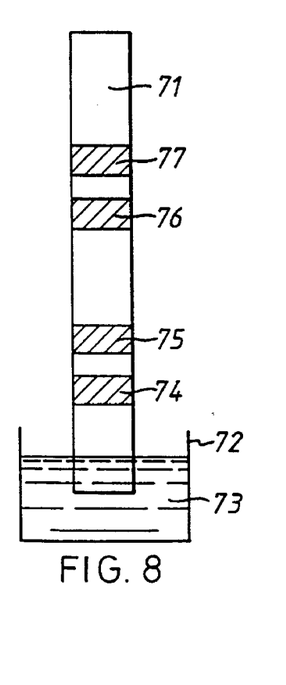
FIG. 8 shows a device for conducting a non-competitive hapten assay.

Referring to FIG. 8 the device comprises a strip of Gelman glass-fibre (15×1 cm), 71, and a reservoir, 72, containing the substrate-buffer, 73. The strip is provided with a sample receiving zone, 74, (1.5 cm from the lower end of the strip), a first reagent zone, 75, (2.0 cm from the lower end of the strip) to which has been applied 10 ul of a monoclonal antibody to PD3G conjugated to peroxidase (1 ug ml$^{-1}$ in Buffer C), a second reagent zone, 76, (5.5 cm from the lower end of the strip) to which has been applied 10 ul of MSA (5,000 nM in Buffer C) and an indicator zone, 77, (6.0 cm from the lower end of the strip) to which has been applied 50 ul of a solid phase monoclonal antibody to El3G.

In use, 20 ul of sample is applied to the sample receiving zone, 74, and the lower end of the strip is placed into 2 ml of substrate-buffer such that only the first 0.5 cm of the strip is immersed. After 15 min, the indicator zone, 77, is observed. The presence of a blue colour at this zone, 77, means that the PD3G concentration in the sample is less than 10000 nM. (colour at 5000 and 10000 nM: no colour at 15000, 20000 and 25000 nM.

The device operates as follows:

As the substrate-buffer migrates along the strip, the PD3G in the sample and the anti-PD3G peroxidase conjugate are transported at the buffer front together with all the components of the buffer-substrate except TMB which exhibits a slower rate of migration (Rf=0.7). During migration along the strip, the anti-PD3G peroxidase binds the PD3G. On reaching the second reagent zone, 76, the MSA in excess binds any unreacted anti-PD3G peroxidase conjugate, and is transported to the indicator zone, 77, where the solid phase anti-El3G antibody binds both free and anti-PD3G peroxidase conjugate bound MSA. Thus, if the concentration of PD3G present in the sample is low, most of the anti-PD3G peroxidase conjugate will be bound by the MSA at the indicator zone, 67. When the TMB reaches the indicator zone, 67, a blue colour will be formed. However, if the concentration of PD3G in the sample is high, then most of the anti-PD3G peroxidase conjugate will be unable to bind the MSA and thus no colour will be observed at the indicator zone, 67.

EXAMPLE 3

A device for conducting a two-site sandwich immunoassay for thyroid stimulating hormone (TSH) such as described generally with reference to FIG. 3 was prepared.

Referring again to FIG. 3, the strip, 21, is Gelman glass-fibre (17×1.8 cm). At the first reagent zone, 25, (5.5 cm from the lower end of the strip) is applied to 20 ul of a monoclonal antibody to TSH conjugated to peroxidase (5 ul ml$^{-1}$ in Buffer C). At the indicator zone, 26, 300 ul of a solid-phase monoclonal antibody to TSH is applied (7.5 cm from the lower end of the strip). In use, 50 ul of sample is applied to the sample receiving zone, 74, and the strip is placed into 5 ml of substrate-buffer such that only the first 1 cm of the strip is immersed. After 15 min, the indicator zone, 26, is observed. The presence of a blue colour indicates that the concentration of TSH present in the sample is greater than 200 mU/L. (No colour at 50, 100 and 200 mU/L: colour at 250 mU/L).

EXAMPLE 4

In another Example of a two-site sandwich assay of the type described generally with reference to FIG. 2, the monoclonal antibodies to TSH described in Example 3 above (at reagent zone 25 and indicator zone 26) were replaced with monoclonal antibodies to human chorionic gonadotrophin. The test can be used as a pregnancy indicator with colour being formed when the urine sample contains more than 200 mIU/Ml hCG. (No colour at 50, 100 and 200 mIU/ml: colour at 250, 300 and 500 mIU/ml).

EXAMPLE 5

A device for conducting a dual analyte assay similar to that described generally with respect to FIG. 4 was prepared.

Figure 9:
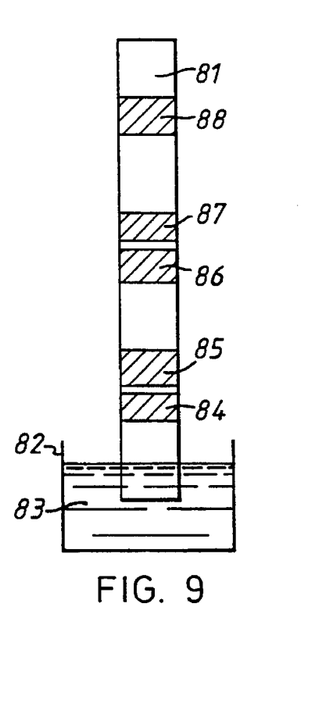
FIG. 9 shows a device for conducting a dual analyte assay.

Referring to FIG. 9 the device comprises of a strip of Gelman glass-fibre (15×1 cm), 81, and a reservoir, 82, containing the substrate-buffer, 83. The strip contains a sample receiving zone, 84, (1.5 cm from the lower end of the strip), a first reagent zone, 85, (2.0 cm from the lower end of the strip) to which has been applied 10 ul of a monoclonal antibody to PD3G conjugated to peroxidase (1 ug ml$^{-1}$ in Buffer C), a third reagent zone, 87, (3.0 cm from the lower end of the strip) to which is applied 10 ul of MSA (250 nM in Buffer C) and an indicator zone, 88, (5.0 cm from the lower end of the strip) to which is applied 50 ul of a solid phase monoclonal antibody to El3G.

In use, 20 ul of a urine sample is applied to the sample receiving zone, 84, and the strip is placed into 2 ml of substrate-buffer such that the lower 0.5 cm of the strip is immersed. After 15 min, the indicator zone, 88, is observed. The presence of a blue colour at this zone, 88, means that the sample concentration of El3G is greater than 50 nM and that the sample concentration of PD3G is less than 10000 nM (see Table 1).

TABLE 1

| E13G (nM) | PD3G (nM) | | | | |
|---|---|---|---|---|---|
| | 0 | 1000 | 5000 | 10000 | 20000 |
| 0 | − | − | − | − | − |
| 50 | − | − | − | − | − |
| 100 | + | + | + | − | − |
| 200 | + | + | + | − | − |

+ = Blue colour at indicator zone.
− = No blue colour at indicator zone.

The device operates as follows:

As the substrate-buffer migrates along the strip, the E13G and PD3G of the sample, anti-PD3G peroxidase conjugate, anti-E13G antibody and MSA migrate at the buffer front with all the components of the buffer-substrate except TMB which exhibits a lower rate of migration (Rf=0.7). If the sample concentration of E13G is low, then the MSA will be bound by the anti-E13G antibody during the migration and will not be bound by the solid phase anti-E13G antibody at the indicator zone, 88. If the E13G level is high, then the MSA is free to bind at the indicator zone, 88. If the PD3G concentration of the sample is low, then the MSA will be bound by the anti-PD3G peroxidase conjugate and thus, when the TMB reaches the indicator zone, 88, a blue colour will be formed. If, however, the PD3G concentration of the sample is high, then it will bind to the anti-PD3G peroxidase conjugate preventing the latter from binding to the MSA and thus no signal will be generated.

It will be understood that the invention has been described by way of example only and modifications of detail may be made within the scope of the invention.

We claim:

1. A test system for performing a binding assay for determining the presence or absence of analyte in a sample or the relative concentrations of two analytes in a sample, comprising:

a) an absorbent material in the form of an elongate strip having a sample application zone upstream of a plurality of transverse reagent zones, wherein said reagent zones of said absorbent material comprise, at least an enzyme-labelled reagent zone which includes an enzyme-labelled species comprising an enzyme-labelled analyte or an enzyme-labelled reagent that binds to said analyte, such that in use, said enzyme-labelled species is caused to migrate through the strip by passage of a developing solution through the strip, and an indicator reagent zone which includes an immobilized reagent that, directly or indirectly, binds and thereby immobilizes said enzyme-labelled species in an amount dependent on the quantity of said analyte present in said sample; and b) a developing solution, wherein said developing solution comprises a signal-producing substrate for the enzyme that generates signal only in or downstream from said indicator reagent zone, wherein the signal-producing substrate is a single color-producing compound or a compound acting as a cofactor with a further compound or compounds to produce a signal in the presence of enzyme, wherein said any further compound or compounds are present in the developing solution;

wherein said developing solution is initially in contact only with that portion of said absorbent material upstream from said indicator zone but in which ultimately, by capillary action, sequentially contacts all reagent zones of said absorbent material;

wherein said enzyme-labelled species is mobilized in said developing solution but does not react with said signal producing substrate to produce color except at or downstream form said indicator reagent zone; and wherein said signal-producing substrate is transported by the developing solution slower than, said enzyme-labelled species.

2. The test system according to claim 1 wherein the developing solution and the signal-producing substrate for the enzyme are contained in a rupturable sac adjoining the absorbent material.

3. The test system according to claim 1 wherein the enzyme is horseradish peroxidase and the developing solution contains tetramethylbenzidine and hydrogen peroxide.

4. The test sheet comprising a rigid plastic backing plate or stand with a plurality of systems according to claim 1 attached thereto.

5. The test system according to claim 1 wherein the enzyme-labelled reagent and the immobilized reagent are antibodies.

6. The test system according to claim 1 wherein the assay is a dual analyte assay for determining the relative concentrations of pregnanediol-3-glucuronide and oestrone-3-glucuronide in urine.

* * * * *